United States Patent [19]

Maligres et al.

[11] Patent Number: 5,229,375
[45] Date of Patent: Jul. 20, 1993

[54] PHOSPHENE OXIDE-TERMINATED ALLENE-ENE-YNE DNA-CLEAVING, ANTITUMOR AND ANTIBIOTIC MOLECULES

[75] Inventors: Peter E. Maligres; Kyriacos C. Nicolaou, both of La Jolla, Calif.

[73] Assignee: Scripps Clinic and Research Foundation, La Jolla, Calif.

[21] Appl. No.: 561,455

[22] Filed: Aug. 1, 1990

[51] Int. Cl.$^5$ .................. C07D 211/04; C07D 215/02; C07D 221/02; C07C 69/007; A61K 31/045; A61K 31/21; A61K 31/33; C07F 9/53

[52] U.S. Cl. .................................. 514/75; 514/82; 514/85; 514/86; 514/89; 514/90; 514/91; 514/94; 514/95; 514/96; 514/99; 514/100; 544/232; 544/243; 544/244; 544/337; 546/22; 546/23; 546/24; 548/112; 548/113; 548/119; 548/413; 548/414; 548/415; 549/5; 549/6; 549/218; 549/220; 560/21; 560/51; 560/59; 560/60; 560/61; 560/64; 560/65; 560/66; 560/81; 568/15

[58] Field of Search ............. 568/17, 15; 514/75, 514/82, 85, 86, 89, 90, 91, 94, 95, 96, 99, 100; 544/232, 243, 244, 337; 546/22, 23, 24; 548/112, 113, 119, 413, 414, 415; 549/5, 6, 218, 220; 560/21, 51, 59, 60, 61, 64, 65, 66, 81

[56] References Cited

U.S. PATENT DOCUMENTS 4,079,125  3/1978  Sipos .................................. 424/32

OTHER PUBLICATIONS

Nicolaou et al., *J. Am. Chem. Soc.*, 110:7247 (1988); "DNA Cleavage by a Synthetic Mimic of the Calicheamicin-Esperamicin Class of Antibiotics".
Nicolaou et al., *Agnew. Chem. Int. Ed. Engl.*, 28:1272 (1989).
Povsic et al., *J. Am. Chem. Soc.*, 111:3059 (1989).
Hertzberg et al., *J. Am. Chem. Soc.*, 104:313 (1982).
Moser et al., *Science*, 238:645 (1987).
Corey et al., *J. Am. Chem. Soc.*, 111:8523 (1989).
Pyle et al., *J. Am. Chem. Soc.*, 111:4520 (1989).
Thederahn et al., *J. Am. Chem. Soc.*, 111:4941 (1989).
Otsuka et al., *J. Am. Chem. Soc.*, 112:838-845 (1990).
Mantlo et al. *J. Org. Chem.*, 54:2781 (1989).
Nagata et al., *Tetrahedron Lett.*, 30:4995 (1989).
Lee et al., *J. Am. Chem. Soc.*, 109:3464 (1987).
Hawley et al.,. *Proc. Natl. Acad. Sci., USA*, 86:1105 (1989).
Golik et al., *J. Am. Chem. Soc.*, 109:3461 (1987).
Edo et al., *Tetrahedron Lett.*, 26:331 (1984).
Chin et al., *Biochemistry*, 27:8106 (1988).
Lee et al., *Biochemistry*, 28:1019 (1989).
Meyers et al., *J. Am. Chem. Soc.*, 111:8057 (1989).
Meyers et al., *J. Am. Chem. Soc.*, 111:9130 (1990).
Kappen et al., *J. Am. Chem. Soc.*, 112:2797 (1990).
Zein et al., *Science*, 240:1198 (1988).
Haseltine et al., *J. Am. Chem. Soc.*, 111:7638 (1989).
Golik et al., *J. Am. Chem. Soc.*, 109:3462 (1987).

*Primary Examiner*—Marianne M. Cintins
*Assistant Examiner*—Margaret J. Page
*Attorney, Agent, or Firm*—Dressler, Goldsmith, Shore, Sutker & Milnamow, Ltd.

[57] ABSTRACT

Phosphine oxide-terminated allene-ene-yne compounds are disclosed that possess DNA-cleaving, antimicobial and tumor growth-inhibiting properties. Methods of making and using those compounds are also disclosed.

11 Claims, 7 Drawing Sheets

Scheme 2
FIG. 2
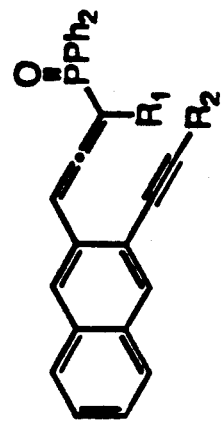
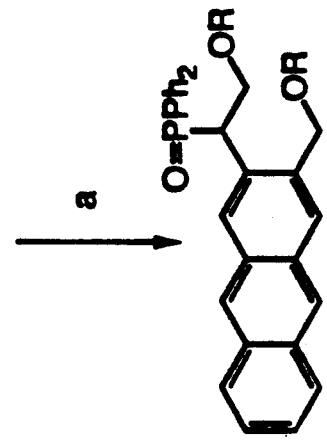
3a: $R_1 = R_2 = CH_2OSi^tBuMe_2$
3b: $R_1 = R_2 = CH_2OH$
18a: R = Si$^t$BuMe$_2$
18b: R = H
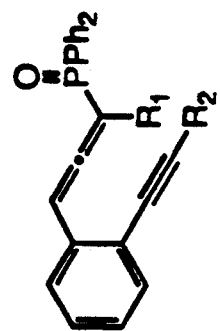
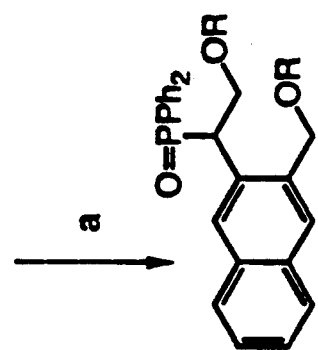
2a: $R_1 = R_2 = CH_2OSi^tBuMe_2$
2b: $R_1 = R_2 = CH_2OH$
17a: R = Si$^t$BuMe$_2$
17b: R = H
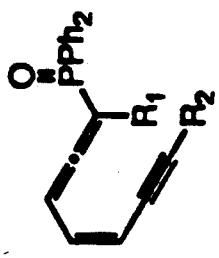
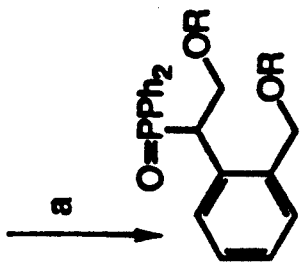
1a: $R_1 = R_2 = CH_2OSi^tBuMe_2$
1b: $R_1 = R_2 = CH_2OH$
4a: $R_1 = CH_2OSi^tBuMe_2, R_2 = Ph$
4b: $R_1 = CH_2OH, R_2 = Ph$
16a: R = Si$^t$BuMe$_2$
16b: R = H

Scheme 3

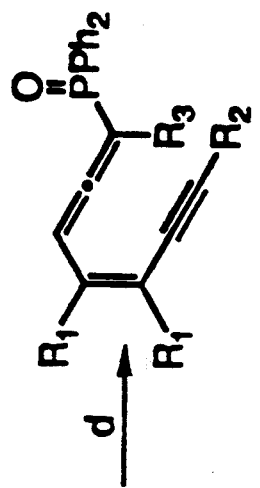

5: $R_1 = H$
6: $R_1 = A$
7: $R_1 = B$ $A = $ phenyl
$B = $ naphthyl
$TBS = Si^tBuMe_2$

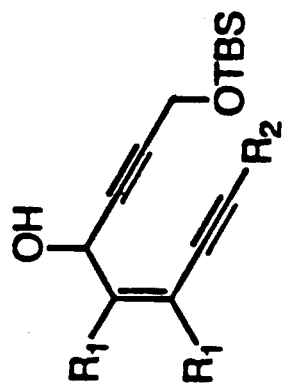

8: $R_1 = H$; $R_2 = CH_2OTBS$ (86%)
9: $R_1 = A$; $R_2 = CH_2OTBS$ (95%)
10: $R_1 = B$; $R_2 = CH_2OTBS$ (98%)
11: $R_1 = H$; $R_2 = Ph$ (72%)

12: $R_1 = H$; $R_2 = CH_2OTBS$ (83%)
13: $R_1 = A$; $R_2 = CH_2OTBS$ (73%)
14: $R_1 = B$; $R_2 = CH_2OTBS$ (73%)
15: $R_1 = H$; $R_2 = Ph$ (67%)

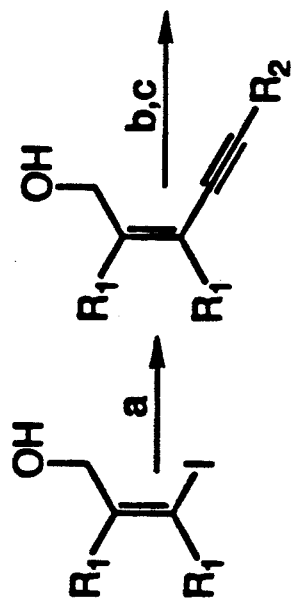

1a: $R_2 = R_3 = CH_2OTBS$; $R_1 = H$ (84%)
1b: $R_1 = H$; $R_2 = R_3 = CH_2OH$ (96%)
2a: $R_2 = R_3 = CH_2OTBS$ $R_1 = A$ (91%)
2b: $R_1 = A$; $R_2 = R_3 = CH_2OH$ (90%)
3a: $R_2 = R_3 = CH_2OTBS$ $R_1 = B$ (76%)
3b: $R_1 = B$; $R_2 = R_3 = CH_2OH$ (93%)
4a: $R_3 = CH_2OTBS$ $R_1 = H$; $R_2 = Ph$ (60%)
4b: $R_1 = H$; $R_2 = Ph$; $R_3 = CH_2OH$ (99%)

PHOSPHENE OXIDE-TERMINATED ALLENE-ENE-YNE DNA-CLEAVING, ANTITUMOR AND ANTIBIOTIC MOLECULES

This invention was made with governmental support under National Institutes of Health Contract CA 46446-03. The Government of the United States of America has certain rights in the invention.

DESCRIPTION

Technical Field

The present invention relates to novel DNA-cleaving, antibiotic and antitumor compounds, and particularly to molecules that contain a phosphene oxide-terminated allene-cis-ene-yne functionality.

Background Art

Natural products have been capturing the interest and imagination of isolation, synthetic, and medicinal chemists for a very long time due to their fascinating structures and biological activities. Man-designed molecules ("designer molecules") with predefined chemical and biological properties could enrich and complement this arsenal of substances, and sharpen the capability of chemistry to deliver biologically and therapeutically useful compounds.

Described herein are the design, synthesis, chemical and biological actions of novel designer molecules with DNA cleaving and antitumor properties; for some recent examples of designed DNA-cleaving molecules, see: (a) Nicolaou et al., *Am. Chem. Soc.*, 110:7247 (1988); (b) Nicolaou et al., *Angew. Chem Int. Ed. Engl.*, 28:1272 (1989); (c) Povsic et al., *J. Am. Chem. Soc.*, 111:3059 (1989); (d) Hertzberg et al., *J. Am. Chem. Soc.*, 104:313 (1982); (e) Moser et al., *Science*, 238:645 (1987); (f) Corey et al., *J. Am. Chem. Soc.*, 111:8523 (1989); (g) Pyle et al., *J. Am. Chem. Soc.*, 111:4520 (1989); (h) Thederahn et al., *J. Am. Chem. Soc.*, 111:4941 (1989); (i) Otsuka et al., *J. Am. Chem. Soc.*, 112:838 (1990; (j) Mantlo et al. *J. Org. Chem. Soc.*, 54:2781 (1989).

In addition, Nagata et al., *Tetrahedron Lett.*, 30:4995 (1989) reported synthesis of a molecule that contained an allene-ene-yne functionality that also contained a phosphene oxide group. That phosphene oxide was bonded to the allene group proximal to the double bond, as compared to the compounds described hereinafter in which the phosphene oxide group is bonded to a terminal position of the allene group, distal to the double bond. No biological studies were reported by Nagata et al.

In addition to the man-made DNA cleaving compounds, naturally occurring ene-diyne compounds have also been reported and studied. Included among the naturally occurring enediynes are calicheamicin and esperimicin that have substantially identical aglycon portions but different sugar portions [(a) Lee et al., *J. Am. Chem. Soc.*, 109:3464, 3466 (1987); (b) Nicolaou et al., *J. Am. Chem. Soc.*, 110:7247 (1988); (c) Hawley et al., *Proc. Natl. Acad. Sci. USA*, 86:1105 (1989); (d) Golik et al., *J. Am. Chem. Soc.*, 109:3461, 3462 (1987)] and neocarzinostation that also contains sugar-derivative side chains [(a) Edo et al., *Tetrahedron Lett.*, 26:331 (1984); (b) Chin et al., *Biochemistry*, 27:8106 (1988); (c) Lee et al., *Biochemistry*, 28:1019 (1989)].

BRIEF SUMMARY OF THE INVENTION

The present invention relates to phosphene oxido-terminated allene-ene-yne compounds that have DNA-cleaving, antimicrobial and tumor growth-inhibiting activites. A compound of the invention is a diphenl(1,-8-disubstituted-octa-2,3,5-trien-7-yne)phosphene oxide having a generalized structure as shown below

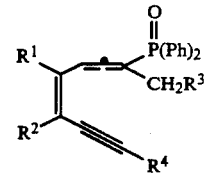

wherein
Ph is phenyl;
$R^1$ and $R^2$ are hydrogen (H) or $R^1$ and $R^2$ together with the unsaturated carbon atoms bonded thereto (the depicted intervening vinylidene group) form a mono- or bicyclic aromatic ring;
$R^3$ is hydroxyl or $C_1$-$C_6$ acyloxy; and
$R^4$ is hydroxymethyl, $C_1$-$C_6$ acyl hydroxymethyl or phenyl.

Where $R^1$ and $R^2$ together with their bonded unsaturated carbon atoms form a mono- or bicyclic aromatic ring, that ring is preferably a benzo or naphtho ring. It is also preferred that $R^3$ be hydroxyl and that $R^4$ be hydroxymethyl or phenyl.

A pharmaceutical composition is also contemplated herein. Here, a before-described compound is dissolved or dispersed in a physiologically tolerable diluent in an amount effective for a desired effect such as DNA cleaving, as an antimicrobial or to inhibit tumor growth.

A method of cleaving DNA, inhibiting tumor growth or killing microbes is also contemplated. Here, a composition as described above is contacted with the DNA to be cleaved, target tumor cells whose growth is to be inhibited or target microbial cells to be killed. That contact is maintained for a time period sufficient for the desired result to be obtained. A composition can be administered repeatedly.

BRIEF DESCRIPTION OF THE DRAWINGS

In the drawings forming a portion of this disclosure,

FIG. 2 shows a reaction scheme (Scheme 2) that illustrates the cyclization reactions of a number of compounds of the invention. In this scheme, Ph is phenyl $R_1$ and $R_2$ are $CH_2R^3$ and $R^4$ as defined hereinafter, and $Si^tBuMe_2$ is t-butyldimethylsilyl.

FIG. 3 shows a reaction scheme (Scheme 3) for the preparation of compounds of the invention via intermediate compounds. Parenthesized percentages are yields in each step shown. R groups are as shown, with Ph and $Si^tBuMe_2$ being as defined before.

DETAILED DESCRIPTION OF THE INVENTION

I. Background

Figure 1:
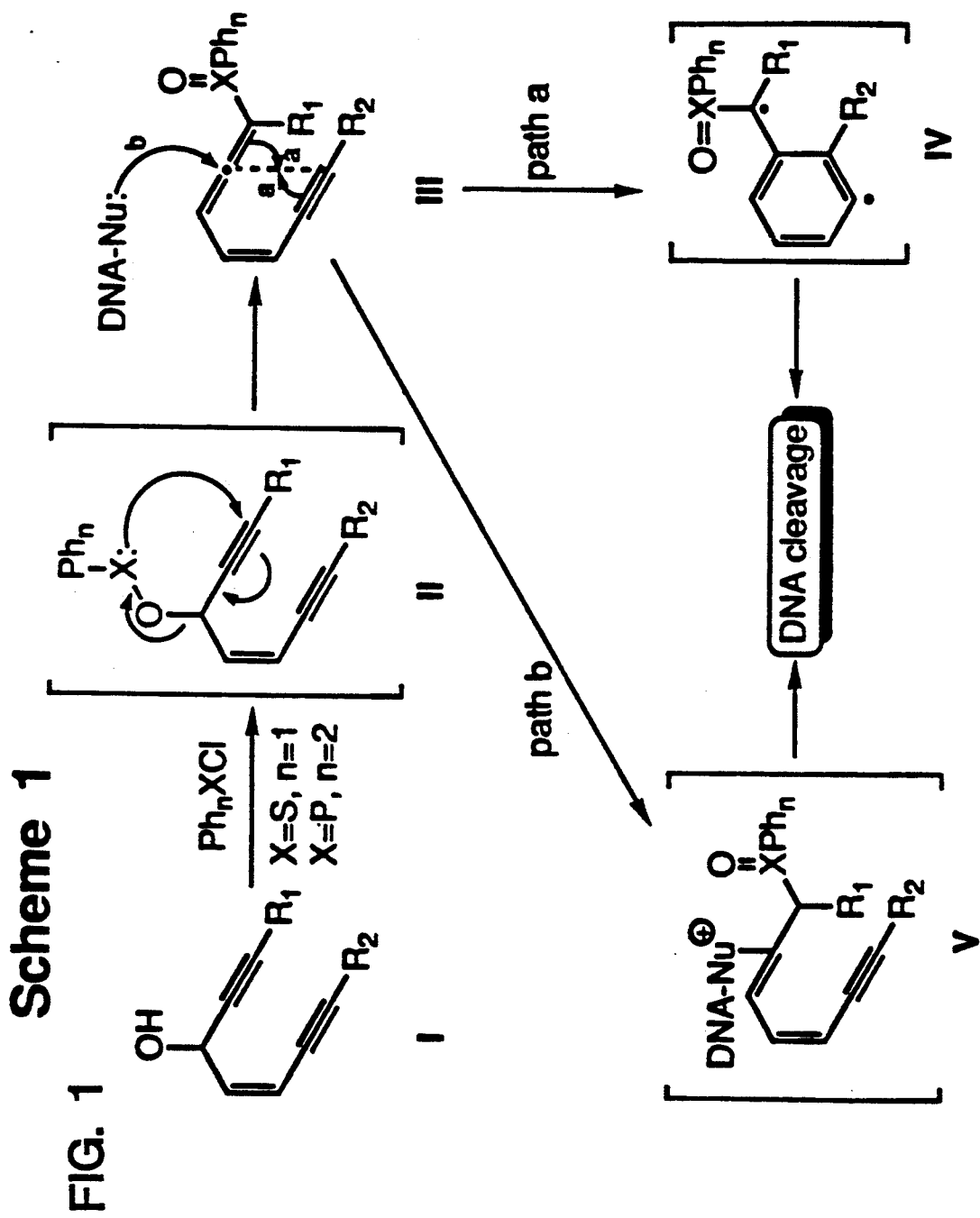
FIG. 1 shows a reaction scheme (Scheme 1) that illustrates a mechanistic rationale for the preparation of a compound of this invention (III) and its reaction in DNA cleavage by paths a or b. In this scheme, $R_1$ and $R_2$ are generalized substituents that are specifically disclosed herein as $CH_2R^3$ and $R^4$, respectively, X is phosphorous or sulfur and n is one for sulfur or two for phosphorous, and Ph is phenyl. Bracketed structures are proposed intermediates, and curved arrows show positions of bond rearrangement and attack by DNA.

Scheme 1 of FIG. 1 depicts the mechanistic rationale for the formation and action of these new class of compounds. Thus, it was hypothesized that propargylic compounds of type I may be induced to rearrange to the conjugated allenic systems III under the influence of PhSCl or Ph$_2$PCl via intermediates II. Structures III were then expected to undergo a Meyers cyclization reaction [(a) Meyers et al., *J. Am. Chem. Soc.*, 111:8057 (1989); (b) Meyers et al., *J. Am. Chem. Soc.*, 111:9130 (1990); (c) Kappen et al., *J. Am. Chem. Soc.*, 112:2797 (1990)] to form radicals IV (path a) or undergo nucleophilic attack originating from DNA to form species V (path b) as expected from recent results with propargylic and allenic sulfones. [Nicolaou et al., *Angew Chem. Int. Ed. Engl.*, 28:1272 (1989)]. Either pathway should cause cleavage of DNA.

Sulfur compounds of type III were found to be rather labile and not suitable for practical DNA, antibiotic or antitumor activity studies. The phosphorus series, however, proved to be easily prepared and handled, and exhibited the properties of DNA cleavage and antitumor activity in the temperature range of 37°-47° C. as discussed herein.

II. The Compounds

A compound of the invention is a diphenyl(1,8-disubstituted-octa-2,3,5-trien-7-yne)phosphene oxide, or a 5(6)-position fused ring derivative thereof. A generalized structure for such a compound is illustrated in structural Formula I shown below:

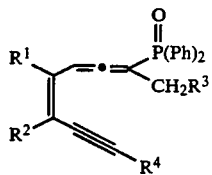

wherein

Ph is phenyl;

$R^1$ and $R^2$ are hydrogen (H) or $R^1$ and $R^2$ together with the unsaturated carbon atoms bonded thereto (intervening vinylidene group) form a mono- or bicyclic aromatic ring;

$R^3$ is hydroxyl or $C_1$-$C_6$ acyloxy; and $R^4$ is hydroxymethyl, $C_1$-$C_6$ acyl hydroxymethyl or phenyl.

It is seen that the allenic and acetylenic groups are in a cis relation to each other. Conversely, it can be said that the 5- and 6-position $R^1$ and $R^2$ groups are in a cis relation about the 5-double bond.

In accordance with the above formula, the 5-position double bond can also be shared with an aromatic ring system that contains one or two fused rings. Those ring systems include substituted and unsubstituted benzene, naphthalene, pyridine, quinoline, isoquinoline, pyrazine, quinoxaline, benzofuran, furan, thiophene, oxazole, pyrimidene, benzothiophene, isobenzofuran, isobenzothiophene, N-$C_1$-$C_6$ alkyl indole, N-$C_1$-$C_6$ alkyl isoindole, N-$C_1$-$C_6$ alkyl benzimidazole and benzoxazole.

A "N-$C_1$-$C_6$ alkyl" group in an above designation is a $C_1$-$C_6$ alkyl group bonded to a secondary nitrogen atom in an appropriate aromatic ring. Exemplary $C_1$-$C_6$ alkyl groups include methyl, ethyl, propyl, isopropyl, butyl, sec-butyl, pentyl, hexyl, 2-methylhexyl, cyclopentyl and cyclohexyl.

An above aromatic ring system can itself also be substituted at one or all of the available positions; i.e., at a position other than those shared with the 5(6)-double bond. Exemplary substituent groups include $C_1$-$C_6$ alkyl, hydroxyl, $C_1$-$C_6$ alkoxy, $C_1$-$C_6$ acyloxy, nitro and halo other than iodo; i.e., fluoro, chloro or bromo.

A before-mentioned $C_1$-$C_6$ acyloxy group is a radical formed by esterification of a hydroxyl group of a before-discussed allene-ene-yne phosphene oxide derivative with a $C_1$-$C_6$ carboxylic acid. Exemplary $C_1$-$C_6$ acyloxy groups include formoxy, acetoxy, propionoxy, hexanoyloxy and cyclopentancarboxy.

Of the above compound types, it is preferred that $R^1$ and $R^2$ be hydrogen, or together with the 5-position double bond (the intervening vinylidene group) form a benzene or naphthalene ring. It is also preferred that $R^3$ be hydroxyl and that $R^4$ be hydroxymethyl or phenyl.

Particularly preferred compounds include:

a) 2-Diphenylphosphoroso-nona-2,3,5-trien-7-yne-1,9-diol; i.e., a compound of Formula I in which $R^1$ and $R^2$ are hydrogen, $R^3$ is hydroxyl and $R^4$ is hydroxymethyl (Compound 1b);

b) 2-Diphenylphosphoroso-8-phenyl-octa-2,3,5-trien-7-yn-1-ol; i.e., a compound of Formula I in which $R^1$ and $R^2$ are hydrogen, $R^3$ is hydroxyl, and $R^4$ is phenyl (Compound 4b);

c) 1-(3-Diphenylphosphoroso-4-hydroxy-3-hydroxyprop-1,2-dienyl)-2-(3-hydroxy-prop-1-ynyl)benzene; i.e., a compound of Formula I in which $R^1$ and $R^2$ together with the intervening double bond form a benzene ring, $R^3$ is hydroxyl, and $R^4$ is hydroxymethyl (Compound 2b); and d) 2-(3-Diphenylphosphoroso-4-hydroxy-but-1,2-dienyl)-3-(3-hydroxy-prop-1-ynyl)naphthalene; i.e., a compound of Formula I in which $R^1$ and $R^2$ together with the intervening double bond form a naphthalene ring, $R^3$ is hydroxyl, and $R^4$ is hydroxymethyl (Compound 3b).

III. Compound Syntheses

A compound of the invention can be readily prepared. A generalized synthetic scheme (Scheme 3) for the preparation of Compounds 1b, 2b, 3b and 4b is shown in FIG. 3. It is noted that subscripted R groups are utilized in Scheme 3 rather than superscripted R groups to differentiate the R groups of the scheme from those superscripted R groups discussed before. The compounds illustrated are nevertheless the same.

Thus, an appropriate hydroxymethylvinyl iodide, e.g., 1-iodo-3-hydroxy-prop-1-ene, 2-iodobenzyl alcohol or 3-iodo-2-naphthyl alcohol (Compounds 5-7), is reacted with a slight excess of an appropriate acetylene derivative such as t-butyldimethylsilyl (TBS) propargyl alcohol or phenylacetylene in the presence of triphenylphospene, palladium$^{II}$ chloride, cuprous iodide and diethylamine to form a conjugated ene-yn-ol (Compounds 8-11).

The alcohol portion of that molecule is oxidized to the corresponding aldehyde as with manganese dioxide. The aldehyde is then reacted with TBS propargyl alcohol in the presence of a strong base such as butyl lithium to form an alcohol containing one double bond and two triple bonds (Compounds 12-15).

Reaction of the enediyne alcohol with chlorodiphenylphosphene forms an O-blocked allene-ene-yne phosphene oxide derivative (Compounds 1a, 2a, 3a and 4a. Removal of the TBS groups as with hydrogen fluoride in acetonitrile forms a desired compound (Compounds 1b, 2b, 3b and 4b).

A starting halo-hydroxymethyl aromatic compound is itself typically a known compound or can be prepared by methods analogous to methods reported in the art. In one exemplary synthesis, a vicinal aromatic amino acid, 3-amino-2-naphthenoic acid, is the starting material for the formation of 3-iodo-2-naphthyl alcohol.

Thus, the carboxyl group is esterified with a convenient $C_1$-$C_6$ alkyl alcohol such as methanol and the ester is reduced to form the hydroxymethyl derivative. A convenient reducing agent is di-isobutylaluminum hydride (DIBAL). Diazotization followed by reaction with an iodide salt such as KI forms the vicinal aromatic hydroxymethyliodide.

Several vicinal aromatic amino acids are available commercially. For example, the Aldrich Chemical Company of Milwaukee, Wis. offers the above aminonaphthoic acid, as well as 2-aminonicotinic acid and 3-amino-pyrazine-2-carboxylic acid and anthranilic acid (2-aminobenzoic acid). Aldrich Chemical also offers 2-iodobenzoic acid.

In addition, several hydroxymethyl compounds are available commercially and need only be suitably halogenated for use herein. For example, all three of the hydroxymethyl pryidines, both hydroxymethyl naphthalenes and indole-3-carbinol, are also available from Aldrich, as is 2-iodobenzyl alcohol.

Hydroxymethyl aromatic compounds can also be prepared from corresponding carboxylic acid esters, as noted before. Staying with the same supplier, Aldrich Chemical Co. offers three quinoline carboxylic acids, two indole carboxylic acids and an indole carboxaldehyde, as well as pyrazine carboxylic acid, and quinoxaline carbonyl chloride, all of which can be esterified and reduced to the corresponding hydroxymethyl compounds, then halogenated and used to form a compound of the invention.

IV. Pharmaceutical Compositions

A compound of the invention is useful as a DNA cleaving agent, and also as an antimicrobial (antibiotic), and a cytoxic (antitumor) agent, as are dynamicin A, calicheamicin, esperimicin and neocarzinostatin. A compound of the invention can also therefor be referred to as an "active agent" or "active ingredient".

DNA cleavage can be assayed using the techniques described hereinafter as well as those described by Mantlo et al., J. Org. Chem., 54:2781 (1989); Nicolaou et al., J. Am. Chem. Soc., 110:7247 (1988) or Zein et al., Science, 240:1198 (1988) and the citations therein. Antimicrobial and antitumor assays can also be carried out by techniques described in U.S. Pat. No. 4,837,206, whose disclosures are incorporated by reference, as well as by the procedures described hereinafter.

A before-described compound can also be shown to undergo a Bergman cycloaromatization reaction in the presence of benzyl mercaptan, triethylamine and 1,4-cycloxadiene as discussed in Haseltine et al., J. Am. Chem. Soc., 111:7638 (1989). This reaction forms a tetracyclic reaction as is formed during DNA cleavage, and can be used as a co-screen to select more active compounds.

A pharmaceutical composition is thus contemplated that contains a before-described compound of the invention as active agent. A pharmaceutical composition is prepared by any of the methods well known in the art of pharmacy all of which involve bringing into association the active compound and the carrier therefor. For therapeutic use, a compound utilized in the present invention can be administered in the form of conventional pharmaceutical compositions. Such compositions can be formulated so as to be suitable for oral or parenteral administration, or as suppositories. In these compositions, the agent is typically dissolved or dispersed in a physiologically tolerable carrier.

A carrier or diluent is a material useful for administering the active compound and must be "pharmaceutically acceptable" in the sense of being compatible with the other ingredients of the composition and not deleterious to the recipient thereof. Thus, as used herein, the phrases "physiologically tolerable" or "pharmaceutically acceptable" are used interchangeably and refer to molecular entities and compositions that do not produce an allergic or similar untoward reaction, such as gastric upset, dizziness and the like, when administered to a mammal. The physiologically tolerable carrier can take a wide variety of forms depending upon the preparation desired for administration and the intended route of administration.

As an example of a useful composition, a compound of the invention (active agent) can be utilized, dissolved or dispersed in a liquid composition such as a sterile suspension or solution, or as isotonic preparation containing suitable preservatives. Particularly well-suited for the present purposes are injectable media constituted by aqueous injectable buffered or unbuffered isotonic and sterile saline or glucose solutions, as well as water alone, or an aqueous ethanol solution. Additional liquid forms in which these compounds can be incorporated for administration include flavored emulsions with edible oils such as cottonseed oil, sesame oil, coconut oil, peanut oil, and the like, as well as elixirs and similar pharmaceutical vehicles. Exemplary further liquid diluents can be found in Remmington's Pharma-

*ceutical Sciences*, Mack Publishing Co., Easton, Pa. (1980).

An active agent can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods of forming liposomes are known in the art. See, for example, Prescott, Ed., *Methods in cell Biology*, Vol. XIV, Academic press, New York, N.Y. (1976), p.33 et seq.

An active agent can also be used in compositions such as tablets or pills, preferably containing a unit dose of the compound. To this end, the agent (active ingredient) is mixed with conventional tableting ingredients such as corn starch, lactose, sucrose, sorbitol, talc, stearic acid, magnesium stearate, dicalcium phosphate, gums, or similar materials as non-toxic, physiologically tolerable carriers. The tablets or pills can be laminated or otherwise compounded to provide unit dosage forms affording prolonged or delayed action.

It should be understood that in addition to the aforementioned carrier ingredients the pharmaceutical formulation described herein can include, as appropriate, one or more additional carrier ingredients such as diluents, buffers, flavoring agents, binders, surface active agents, thickeners, lubricants, preservatives (including antioxidants) and the like, and substances included for the purpose of rendering the formulation isotonic with the blood of the intended recipient.

The tablets or pills can also be provided with an enteric layer in the form of an envelope that serves to resist disintegration in the stomach and permits the active ingredient to pass intact into the duodenum or to be delayed in release. A variety of materials can be used for such enteric layers or coatings, including polymeric acids or mixtures of such acids with such materials as shellac, shellac and cetyl alcohol, cellulose acetate phthalate, and the like. A particularly suitable enteric coating comprises a styrene-maleic acid copolymer together with known materials that contribute to the enteric properties of the coating. Methods for producing enteric coated tablets are described in U.S. Pat. No. 4,079,125 to Sipos, which is herein incorporated by reference.

The term "unit dose", as used herein, refers to physically discrete units suitable as unitary dosages for administration to warm blooded animals, each such unit containing a predetermined quantity of the agent calculated to produce the desired therapeutic effect in association with the pharmaceutically acceptable diluent. Examples of suitable unit dosage forms in accord with this invention are tablets, capsules, pills, powder packets, granules, wafers, cachets, teaspoonfuls, dropperfuls, ampules, vials, segregated multiples of any of the foregoing, and the like.

A compound of the invention is present in such a pharmaceutical composition in an amount effective to achieve the desired result. For example, where in vitro DNA cleavage is the desired result, a compound of the invention can be utilized in an amount sufficient to provide a concentration of about 1.0 to about 5000 micromolar ($\mu$M) with a DNA concentration of about 0.02 $\mu$g/$\mu$L. As a cytoxic (antitumor) agent, an effective amount of a compound of the invention is about 0.1 to about 15 mg per kilogram of body weight or an amount sufficient to provide a concentration of about 0.01 to about 50 $\mu$g/mL to the bloodstream. A compound of the invention exhibits antimicrobial activity in a concentration range of about 0.01 to about 50 $\mu$g/mL. The above concentrations and dosages vary with the particular compound of the invention utilized as well as with the target, e.g., DNA, tumor, microbe, as is well known.

V. Methods

A compound of the invention is useful in cleaving DNA, as an antimicrobial and also in inhibiting the growth of neoplastic cells, and is utilized in a method for effecting such a result. A compound of the invention is typically utilized in a before-described composition.

In accordance with such a method, DNA or target cells to be killed or whose growth is to be inhibited are contacted with a composition that contains a compound of the invention (active ingredient) present in an amount effective or sufficient for such a purpose, as discussed before, dissolved or dispersed in a physiologically tolerable (pharmaceutically acceptable) diluent. That contact is maintained for a time sufficient for the desired result to be obtained; i.e., DNA cleaved, cells killed or neoplastic cell growth inhibited.

Where the desired result is carried out in vitro, contact is maintained by simply admixing the DNA or target cells with the composition and maintaining them together under the appropriate conditions of temperature and for cell growth to occur, as for control, untreated cells. Thus, a single admixing and contacting is typically sufficient for in vitro purposes.

The above method is also useful in vivo, as where a mammal such as a rodent like a rat, mouse, or rabbit, a farm animal like a horse, cow or goat, or a primate like a monkey, ape or human is treated. Here, contact of a composition and the cells to be killed or whose growth is to be inhibited is achieved by administration of the composition to the mammal by oral, nasal or anal administration or by introduction intravenously, subcutaneously or intraperitoneally. Thus, contact in vivo is achieved via the blood or lymph systems.

Although a single administration (admixture) and its resulting contact is usually sufficient to maintain the required contact and obtain a desired result in vitro, multiple administrations are typically utilized in vivo. Thus, because of a body's breakdown and excreting pathways, contact between an active ingredient of a composition and the target cells is typically maintained by repeated administration of a compound of the invention over a period of time such as days, weeks or months, or more, depending upon the target cells.

Exemplary methods of the invention for DNA cleavage and inhibition of MIA PaCa-2 human pancreatic carcinoma (ATCC CRL 1420) target cells as described hereinafter.

VI. Results

Compounds 1a,b-4a,b (Scheme 2 of FIG. 2) were designed and synthesized as summarized in Scheme 3 shown in FIG. 3. The key operations involved: (a) vinyl iodide-acetylene couplings via Pd(Cl)$_2$-Cu(I) catalysis (step a, Scheme 3); (b) acetylide addition to aldehydes (step c, Scheme 3); and, (c) 2,3-sigmatropic rearrangements (step d, Scheme 3).

Compounds 1a, 2a and 3a were sufficiently stable for isolation, but smoothly cyclized to aromatic systems, presumably via diradicals, upon warming in the presence of cyclohexadiene (Scheme 2, step a). The half-lifes ($t_{\frac{1}{2}}$), of these systems at 37° C. (1a: $t_{\frac{1}{2}}=21$ hours; 2a: $t_{\frac{1}{2}}=23$ hours; 3a: $t_{\frac{1}{2}}=60$ hours) indicated that they or their derivatives may be good DNA and tumor cell damaging agents with prolonged periods of action.

Figure 4A:
FIG. 4 in three panels (FIG. 4a, 4b and 4C) are photographs of ethidium bromide stained 1 percent agarose gels that illustrate cleavage of φX174 form I DNA by compounds of the invention after 48 hours at the temperatures shown. Lane 1 of each panel is the starting DNA. Lanes 2-5 of each panel contained Compounds 1b, 2b, 3b and 4b, respectively, present at 1000 μM at a pH value of 8.5. The numerals I, II and III to the left of FIG. 4a show the migration positions of DNA forms I, II and III, respectively.
Figure 4B:
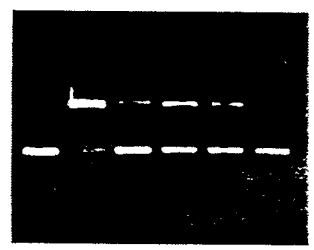
Figure 4C:
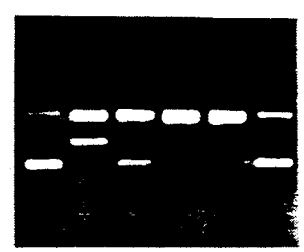

Indeed, Compounds 1b–4b exhibited DNA cleaving properties at 37° C., 42° C. and 47° C. in the absence of any additives. Thus, incubation of Compounds 1b–4b (1000 μM) with supercoiled DNA (form 1) aerobically at pH 8.5 and at various temperatures caused DNA rupture leading, initially to form II and finally to form III DNA, as shown in FIG. 4.

Figure 5:
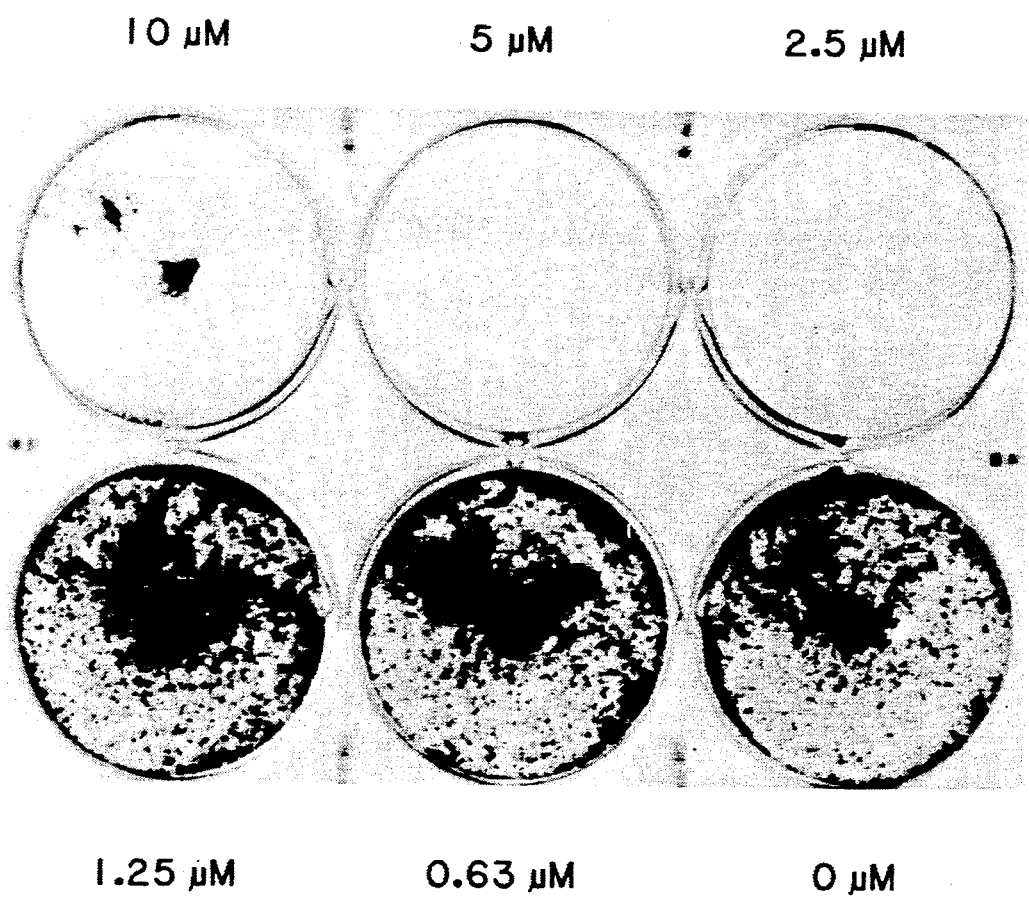
FIG. 5 is a photograph of crystal violet stained cell cultures of MIA PaCa-2 human pancreatic carcinoma cells that illustrate the inhibition of growth after four days of those cells by the shown concentrations, of Compound 4b.
Figure 6:
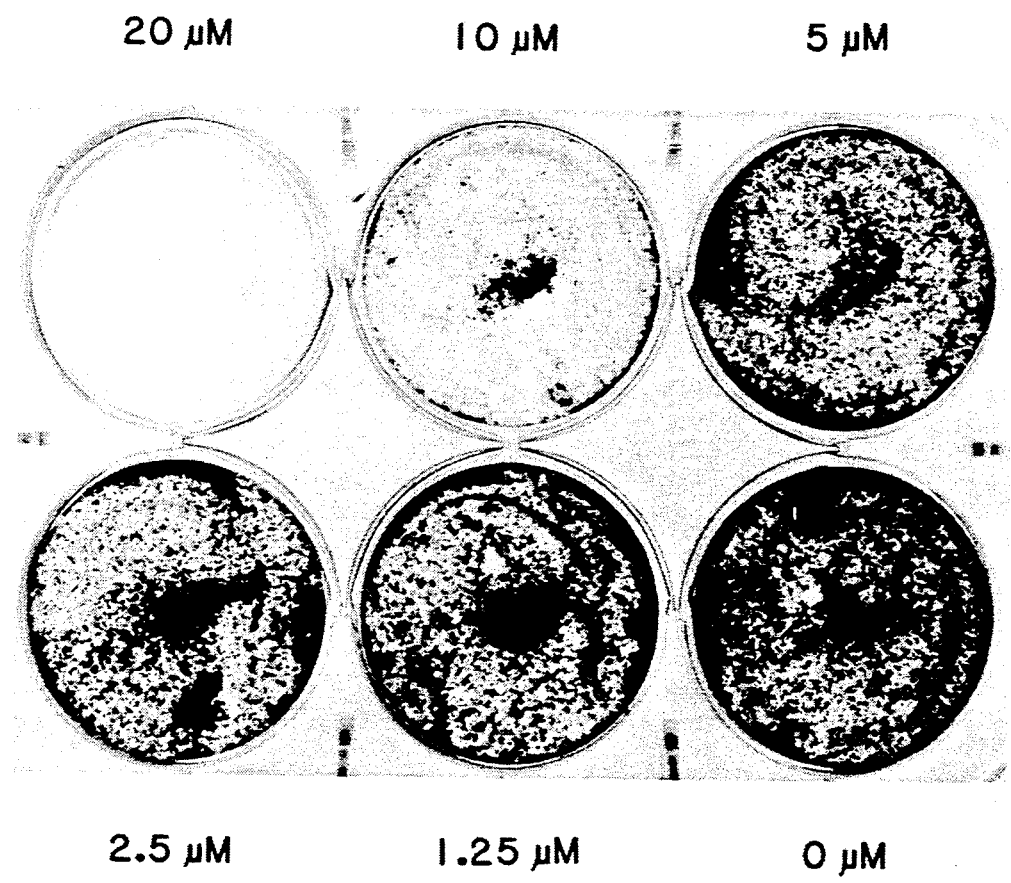
FIG. 6 shows results similar to those of FIG. 5 using Compound 1b.
Figure 7:
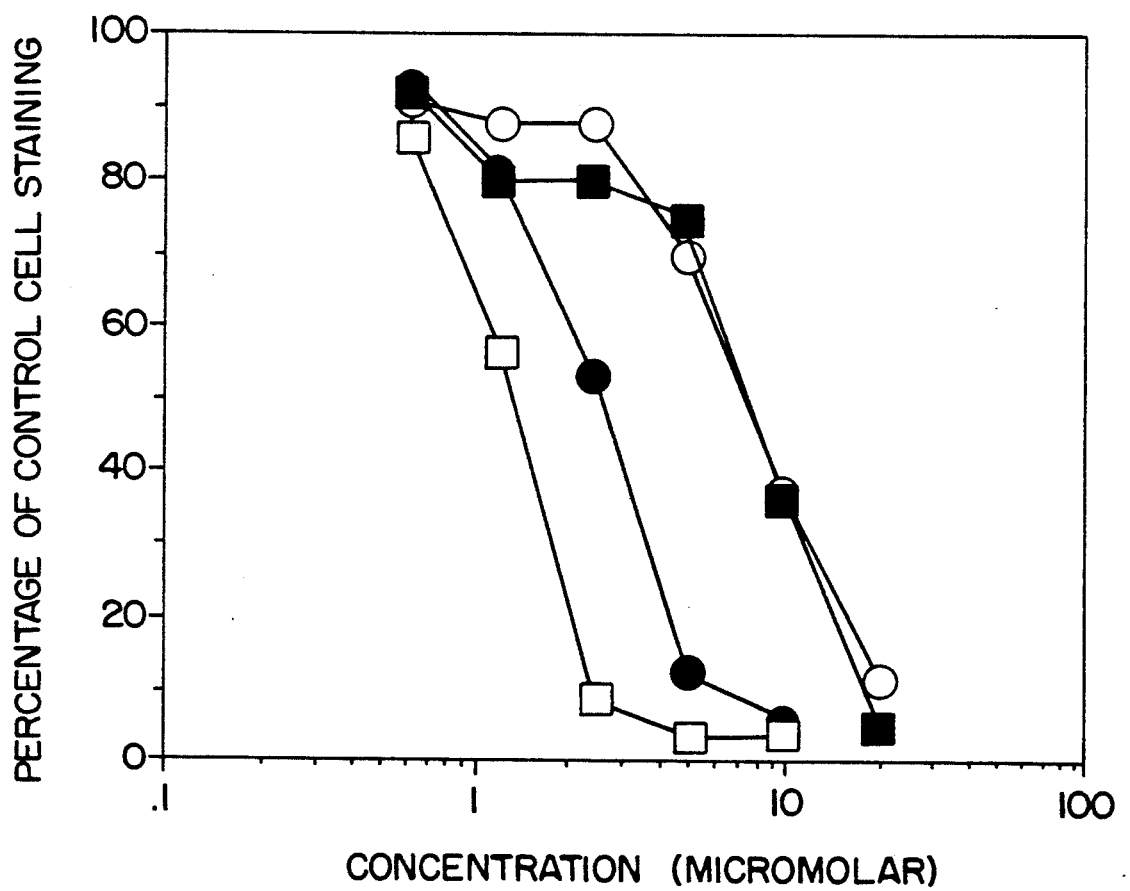
FIG. 7 is a graph that shows the percentage of control cell staining of MIA PaCa-2 human pancreatic carcinoma cells after four days of growth in the presence of Compounds 1b-4b. In this graph, data points are shown as follows: Compound 1b=solid squares; Compound 2b=open Circles; Compound 3b=closed circles; and Compound 4b=open squares.

The anticancer activity of these compounds was assayed using human tumor cells. As can be seen from FIGS. 5, 6 and 7 Compounds 1b–4b exhibited potent, concentration-dependent cytotoxicity against human carcinoma cells thus fulfilling the initial expectations that led to the design of these systems. The potency of these compounds as antitumor agents may increase with temperature elevation as suggested from the higher degree of DNA cleavage (FIG. 4), and thus, selective tissue damage may become possible with these agents via diathermia techniques.

BEST MODE FOR CARRYING OUT THE INVENTION

Assay Methods

DNA Cleavage Studies

To a vial containing a 50 micromolar per base pair solution of φX174 form I double-stranded DNA in 2.0 microliters of pH 8.5 phosphate buffer (50 μM) were added 6.0 microliters of the same buffer solution and 2.0 microliters of a 5.0 millimolar ethanol solution of a compound to be assayed.

The vials were then placed in an oven at the temepratures shown for 48 hours. A 2.0 microliter portion of glycerol loading buffer solution containing bromothymol blue indicator was added to each vial. A 10 microliter aliquote was then drawn from each. Gel electrophoresis analysis of the aliquots was performed using a 2.0 percent agarose getl with ethidium bromide run at 115 volts for 1 hour. DNA cleavage was indicated by the formation of form II or III DNA, which was detected by visual inspection of the gel under 310 nanometer ultraviolet light.

Procedure for 6-Well Cytotoxicity Assay

MIA PaCa-2 human pancreatic carcinoma cells were loaded into each well of a 6-well plate at a density of 100,000 cells/well in 3 ml culture medium. They were incubated for 4 hours (37° C., 7 percent $CO_2$). Then 6 microliters of the cytotoxin solution was added into 3 ml of medium (RPMI-1640, with 5 percent fetal bovine serum and 1 percent glutamine) in a 500×dilution so that in one well ethanol was added to make a 0.2 percent ethanol control. The plates were then incubated for 4 days (37° C., 7 percent $CO_2$). The medium was then drained, crystal violet dye (Hucker formula) was added to cover the well bottoms and then they were rinsed with tap water until rinses were clear. The stained cells were solubilized for quantitation with Sarkoscyl solution (N-Lauryl sarcosine, 1 percent in water) at 3 ml/well. The absorbance of the solution was then read at 590–650 nm.

EXAMPLE 1

Compound 8

To a stirred solution of 1.93 g (10.5 mmol) of the vinyl iodide Compound 5 and 1.70 g (10.0 mmol) of the terminal alkyne (here the TBS ether of propargyl alcohol) in 20 dry benzene under argon at room temperature were added via syringe 1.54 mL (15.0 mmol) of diethylamine. Immediately afterwards, 0.28 g (0.40 mmol) of bis-triphenylphosphine palladium dichloride and 0.31 g (1.60 mmol) of cuprous iodide were introduced as solids. Stirring was continued for 1 hour at room temperature. Then 30 mL of saturated aqueous ammonium chloride were added, and the mixture was stirred in air for 1 hour. To this, 30 mL of ether were added and the upper organic layer was dried over magnesium sulfate, filtered, and concentrated. The residue was purified by flash chromatography (silica) eluting with 30 percent ether in petroleum ether to give 1.95 g of product Compound 8 in 86 percent yield.

EXAMPLE 2

Compound 12

To a solution of 1.00 g (4.42 mmol) of the eyn-allylic alcohol Compound 8 in 20 mL of dry benzene at room temperature were added 7.00 g (80.5 mmol) of activated manganese dioxide and the mixture was stirred at room temperature for 24 hours. The mixture was filtered through celite, and the filter cake was washed with 60 mL of tetrahydrofuran. The filtrates were concentrated to give 0.84 g of the aldehyde in 84 percent yield.

6.13 milliliters (9.84 mmol) of 1.6M n-butyllithium in hexanes were added by syringe to a stirred solution of 1.97 g (11.59 mmol) of the t-butyldimethylsilyl (TBS) ether of propargyl alcohol in 40 mL tetrahydrofuran under an argon atmosphere cooled to −78° C. Stirring was continued for 30 minutes, while allowing the temperature to rise to −10° C. The reaction mixture was cooled to −20° C. and a solution of 2.00 g (8.91 mmol) of the aldehyde in 10 mL of tetrahydrofuran was added dropwise by syringe over 5 minutes. After stirring for 1 hour, 100 mL of saturated aqueous ammonium chloride and 50 mL of ether was added. The upper organic layer was dried over magnesium sulfate, filtered, and concentrated. The residue was purified by flash chromatography (silica) eluting with 25 percent ether alcohol in petroleum ether to give 3.48 g of product ene-diyne alcohol Compound 12 in 99 percent yield.

Pale yellow oil; $R_f$=0.48 (silica, 30 percent ether in petroleum ether); $^1$H NMR (500 MHz, $CDCl_3$) δ 5.98 (dd, J=10.6, 8.8 Hz, 1 H, =CH—CHOH), 5.65 (dt, J=10.6, 2.0 Hz, 1 H, ≡C—CH=CH), 5.41 (bd, J=8.8 Hz, 1 H, =CH=CHOH), 4.46 (bd, J=2.0 Hz, 2 H, $CH_2O$), 4.35 (d, J=1.8 Hz, 2 H, $CH_2O$), 0.91 (s, 9 H, Si$^t$BuMe$_2$), 0.90 (s, 9 H Si$^t$BuMe$_2$), 0.13 (s, 6 H, Si$^t$-BuMe$_2$), 0.11 (s, 6 H, Si$^t$BuMe$_2$), IR ($CHCl_3$) $v_{max}$ 3596, 2957, 2931, 2859, 1472, 1364, 1257, 1128, 1077, 838 cm$^{-1}$; $^{13}$C NMR (125 MHz, $CDCl_3$ δ 140.4 (=CH—CHOH), 111.0 (=CH—CHOH), 52.1 ($CH_2O$), 51.7 ($CH_2O$), 25.8 (Si$^t$BuMe$_2$), 18.2 (Si$^t$BuMe$_2$), −5.2 (Si$^t$-BuMe$_2$); UV (EtOH) $\lambda_{max}$ 230 nm (ε 11,500).

EXAMPLE 3

Compound 1a

To a stirred solution of 1.00 g (2.53 mmol) of the ene-diyne alcohol in 35 mL of dry methylene chloride, cooled to −78° C., were added via syringe 0.39 mL (2.79 mmol) of triethylamine followed by 0.50 mL (2.79 mmol) chlorodiphenylphosphine. Stirring was continued for 1 hour and 50 mL of saturated aqueous ammonium chloride were added. The lower organic layer was dried over magnesium sulfate, filtered and concentrated. The residue was purified by flash chromatography (silica) eluting with 80 percent ether in petroleum ether to give 1.23 g of the phosphine oxide Compound 1a in 84 percent yield.

Pale yellow oil, $R_f$=0.40 (silica, ether); $^1$H NMR (500 MHz, CDClD$_3$) δ 7.78–7.67 (m, 4 H, aromatic), 7.53–7.40 (m, 6 H, aromatic), 6.43 (ddtd, J=10.7, 10.7, 2.7, 1.0 Hz, 1 H, CH=C=), 6.03 (ddd, J=10.7, 10.7, 1.8 Hz, 1 H, CH=CH—CH=), 5.35 (dm, J=10.7 Hz, 1 H, =C—CH=CH—), 4.50 (m, 2 H, =C(P=O)—CH$_2$O), 4.45 (d, J=2.0, 2 H, ≡C—CH$_2$O), 0.90 (s, 9 H, Si$^t$BuMe$_2$), 0.79 (s, 9 H, Si$^t$BuMe$_2$), 0.11 (s, 3 H, Si$^t$BuMe$_2$), 0.10 (s, 3 H, Si$^t$BuMe$_2$), −0.03 (s, 6 H, Si$^t$BuMe$_2$); IR (CHCl$_3$) $\nu_{max}$ 2957, 2931, 2858, 1931, 1603, 1471, 1438, 1258, 1171, 1119, 1098, 839 cm$^{-1}$; $^{13}$C NMR (125 MHz, CDCl$_3$) δ 212.4 ($^2$Jccp=4.4 Hz, CH=C=C), 132.8–128.1 (thirteen overlapping signals, aromatic, ≡C—CH=), 109.7 ($^4$Jccccp=4.9 Hz, C=CH—CH=), 101.8 ($^1$Jcp=98.5 Hz, CH=C=C), 95.6 (acetylene), 94.9 ($^3$Jcccp=13.0 Hz, CH=C=C), 80.7 (acetylene), 60.3 ($^2$Jccp=10.5 Hz, =C(P=O)—CH$_2$O), 52.1 (≡C—CH$_2$O), 25.7 (Si$^t$BuMe$_2$), 25.6 (Si$^t$BuMe$_2$), 18.1 (Si$^t$BuMe$_2$), −5.2 (Si$^t$BuMe$_2$), −5.6 (Si$^t$BuMe$_2$); UV (EtOH) λ$_{max}$ 274 (ε 10,500), 267 (ε 10,500), 222 nm (ε 28,000); HRMS calcd for C$_{33}$H$_{48}$O$_3$PSi$_2$ (M⊕+1): 579.2879, found: 579.2877.

EXAMPLE 4

Compound 1b 0.10 Milliliters of 48 percent aqueous hydrofluoric acid were added to a solution of 34.7 mg (0.0599 mmol) of the phosphine oxide Compound 1a in 1.0 mL of acetonitrile at room temperature. After stirring for 15 minutes, the solvents were pumped off at 0.01 torr. The residue was dissolved in 1.0 mL of chloroform and the solvent was again pumped off to give 20.2 mg of the diol in Compound 1b in 96 percent yield.

Pale yellow oil, $R_f$=0.27 (silica, ethyl acetate); $^1$H NMR (500 MHz, CDCl$_3$) δ 7.77–7.40 (m, 10 H, aromatic), 6.08 (dd, J=10.4, 10.4 Hz, 1 H, CH=C=), 5.77 (dd, J=10.4, 10.4 Hz, 1 H, =CH—CH=C=), 5.52 (dm, J=10.4 Hz, 1 H, =C—CH=CH—), 4.44 (m, 4 H, —CH$_2$OH), 3.4 (bs, 2 H, OH); IR (neat) $\nu_{max}$ 3318, 2971, 2950, 2871, 1928, 1438, 1169, 1120 cm$^{-1}$; UV (EtOH) λ$_{max}$ 274 (ε 18,500), 222 nm (sh, e 26,500); HRMS calcd for C$_{21}$H$_{19}$O$_3$PCs (M⊕+Cs): 483.0126, found: 483.0126.

EXAMPLE 5

Compound 16a

A solution of 123 mg (0.212 mmol) of the ene-yne-allene Compound 1a in 5.0 mL of 1,4-cyclohexadiene was stirred at 37° C. for 35 hours and then concentrated. Preparative TLC (silica, 0.5 mm×20×20 cm) eluting with 80 percent ether in petroleum ether gave 74 mg of the cyclized product Compound 16a in 60 percent yield.

Pale yellow oil, $R_f$=0.43 (silica, ethyl acetate); $^1$H NMR (500 MHz, CDCl$_3$) δ 7.97 (dd, J=7.7, 1.6 Hz, 1 H, aromatic), 7.94 (dd, J=7.8, 1.6 Hz, 1 H, aromatic), 7.84 (d, J=7.4 Hz, 1 H, aromatic), 7.58–7.50 (m, 5 H, aromatic), 7.28 (m, 1 H, aromatic), 7.21–7.13 (m, 5 H, aromatic), 4.75 (d, J=12.0 Hz, 1 H, Ar—CH$_2$O), 4.57 (d, J=12.0 Hz, 1 H, Ar—CH$_2$O), 4.34 (m, 2 H, Ar—CH(P=O), CH—CH$_2$O), 4.14 (m, 1 H, CH—CH$_2$O), 1.01 (s, 9 H, Si$^t$BuMe$_2$), 0.69 (s, 9 H, Si$^t$BuMe$_2$), 0.17, 0.16, −0.20, −0.26 (singlets, 3 H each, Si$^t$BuMe$_2$); IR (CHCl$_3$) $\nu_{max}$ 2957, 2930, 2858, 1471, 1438, 1257, 1117, 1101, 838 cm$^{-1}$; $^{13}$C NMR (125 MHz, CDCl$_3$) δ 139.1–126.9 (several signals, aromatic), 64.7 (CH$_2$O), 64.3 (CH$_2$O), 43.9 ($^1$Jcp=67.9 Hz, Ar—CH(P=O), 26.1 (Si$^t$BuMe$_2$), 25.7 (Si$^t$BuMe$_2$), 18.6 (Si$^t$BuMe$_2$), 18.1 (Si$^t$BuMe$_2$), −5.1, −5.2, −5.8, −5.9 (Si$^t$BuMe$_2$); UV (EtOH) λ$_{max}$ 266 nm (ε 3,500); HRMS calcd for C$_{33}$H$_{50}$O$_3$PSi$_2$ (M⊕+1): 581.3036, found: 581.3012.

EXAMPLE 6

Compound 16b 0.10 Milliliters of 48 percent aqueous hydrofluoric acid were added to a solution of 112 mg (0.193 mmol) of the cyclized product Compound 16a in 1.0 mL of acetonitrile at room temperature. After stirring for 15 minutes, the solvents were pumped off at 0.01 torr. The residue was dissolved in 1.0 mL of chloroform and the solvent was again pumped off to give 68 mg of the diol in Compound 16b in quantitative yield.

Compound 6 was purchased from Aldrich Chemical Co., Milwaukee, Wis. Compounds 9, 13, 2a, 2b and 17a were prepared in manners substantially similar to the methods utilized for preparing Compounds 8, 12, 1a, 1b and 16a. Data relating to Compounds 13, 2a, 2b and 17a are provided below.

Compound 13

Pale yellow oil, $R_f$=0.50 (silica, 30 percent ether in petroleum ether); $^1$H NMR (300 MHz, CDCl$_3$) δ 7.70 (d, J=7.7 Hz, 1 H, aromatic), 7.45–7.27 (m, 3 H, aromatic), 5.91 (bs, 1 H, CHOH), 4.59 (s, 2 H, Ar—C≡C—CH$_2$O), 4.40 (d, J=1.6 Hz, 2 H, CHOH—C≡C—CH$_2$O), 2.58 (bs, 1 H, OH), 0.95 (s, 9 H, Si$^t$BuMe$_2$), 0.90 (s, 9 H, Si$^t$BuMe$_2$), 0.18 (s, 6 H, Si$^t$BuMe$_2$), 0.11 (s, 6 H, Si$^t$BuMe$_2$); IR (CHCl$_3$) $\nu_{max}$ 3595, 2957, 2931, 2859, 1472, 1365, 1256, 1079, 838 cm$^{-1}$; $^{13}$C NMR (125 MHz, CDCl$_3$) δ 142.1 (aromatic), 132.5 (aromatic), 128.8 (aromatic), 128.2 (aromatic), 126.7 (aromatic), 121.1 (aromatic), 93.2 (acetylene), 85.3 (acetylene), 83.8 (acetylene), 82.0 (acetylene), 62.9 (CHOH), 52.2 (CH$_2$O), 51.8 (CH$_2$O), 25.8 (Si$^t$BuMe$_2$), 18.3 (Si$^t$BuMe$_2$), 18.2 (Si$^t$BuMe$_2$), −5.1 (Si$^t$BuMe$_2$), −5.2 (Si$^t$BuMe$_2$); UV (EtOH) λ$_{max}$ 244 (ε 13,000), 209 nm (ε 28,000).

Compound 2a

Pale yellow oil, $R_f$=0.40 (silica, ether); $^1$H NMR (300 MHz, CDCl$_3$) δ 7.97–7.81 (m, 4 H, aromatic), 7.66–7.39 (m, 8 H, aromatic), 7.30–7.21 (m, 2 H, aromatic), 6.91 (dt, J=10.6, 2.9 Hz, 1 H, CH=C=), 4.72 (m, 2 H, =C(P=O)—CH$_2$O), 4.66 (s, 2 H, ≡C—CH$_2$O), 1.06 (s, 9 H, Si$^t$BuMe$_2$), 0.90 (s, 9 H, Si$^t$BuMe$_2$), 0.27 (s, 6 H, Si$^t$BuMe$_2$), 0.09 (s, 6 H, Si$^t$BuMe$_2$); IR (CHCl$_3$) $\nu_{max}$ 2958, 2931, 2858, 1938, 1487, 1438, 1363, 1256, 1181, 1120, 1098, 838 cm$^{-1}$; $^{13}$C NMR (125 MHz, CDCl$_3$) δ 210.3 ($^2$J$_{ccp}$=5.3 Hz, CH=C=C), 133.9 ($^4$J$_{ccccp}$=6.8 Hz, aromatic), 132.5–120.7 (sixteen signals, aromatic), 103.8 ($^1$J$_{cp}$=99.2 Hz, CH=C=C), 96.2 ($^3$J$_{cccp}$=12.9 Hz, CH=C=C), 92.8 (acetylene), 82.4 (acetylene), 60.5 ($^2$J$_{ccp}$=10.8 Hz, =C(P=O)—CH$_2$O), 52.2 (=C—CH$_2$O), 25.8 (Si$^t$BuMe$_2$), 25.7 (Si$^t$BuMe$_2$), 18.3 (Si$^t$BuMe$_2$), 18.2 (Si$^t$BuMe$_2$), −5.1 (Si$^t$BuMe$_2$), −5.5 (Si$^t$BuMe$_2$); UV (EtOH) λ$_{max}$ 274 (ε 23,000), 223 nm (ε 37,000); HRMS calcd for C$_{37}$H$_{50}$O$_3$PSi$_2$ (M⊕+1): 629.3036, found: 629.3081.

Compound 2b

Pale yellow oil, R$_f$=0.27 (silica, ethyl acetate); $^1$H NMR (500 MHz, CDCl$_3$) δ 7.82 (m, 2 H, aromatic), 7.67 (m, 2 H, aromatic), 7.58 (m, 1 H, aromatic), 7.52 (m, 2 H, aromatic), 7.37 (m, 2 H, aromatic), 7.26 (m, 2 H, aromatic), 7.14 (m, 2 H, aromatic), 6.89 (m, 1 H, aromatic), 6.33 (dt, J=10.8, 2.2 Hz, 1 H, CH=C=), 4.59 (d, J=16.7 Hz, 1 H, ≡C—CH$_2$O), 4.50 (d, J=16.7 Hz, 1 H, ≡C—CH$_2$O), 4.49 (m, 2 H, =C(P=O)—CH$_2$O); IR (CHCl$_3$) ν$_{max}$ 3307, 3011, 2929, 2856, 1936, 1438, 1220, 1160, 1120, 1028 cm$^{-1}$; $^{13}$C NMR (125 MHz, CDCl$_3$) δ 211.1 ($^2$J$_{ccp}$=5.9 Hz, CH=C=C), 134.0–127.6 (fifteen signals, aromatic), 121.4 (aromatic), 101.4 ($^1$J$_{cp}$=99.2 Hz, CH=C=C), 96.6 ($^3$J$_{cccp}$=13.1 Hz, CH=C=C), 95.8 (acetylene), 83.5 (acetylene), 61.2 ($^2$J$_{ccp}$=7.2 Hz, =C(P=O)—CH$_2$OH), 51.4 (≡C—CH$_2$OH); UV (EtOH) λ$_{max}$ 267 (sh, ε 7,200), 226 nm (ε 31,000); HRMS calcd for C$_{25}$H$_{21}$O$_3$PCs (M⊕+Cs): 533.0282, found: 533.0274.

Compound 17a

Pale yellow oil, R$_f$=0.44 (silica, ethyl acetate); $^1$H NMR (500 MHz, CDCl$_3$) δ 8.30 (bs, 1 H, aromatic), 7.94 (m, 2 H, aromatic), 7.80 (m, 1 H, aromatic), 7.72 (m, 1 H, aromatic), 7.64 (s, 1 H, aromatic), 7.52 (m, 5 H, aromatic), 7.40 (m, 2 H, aromatic), 7.18 (m, 1 H, aromatic), 7.10 (m, 2 H, aromatic), 4.87 (d, J=12.1 Hz, 1 H, Ar—CH$_2$O), 4.72 (d, J=12.1 Hz, 1 H, Ar—CH$_2$O), 4.43 (m, 2 H, Ar—CH(P=O), CH—CH$_2$O), 4.20 (m, 1 H, CH—CH$_2$O), 1.00 (s, 9 H, Si$^t$BuMe$_2$), 0.64 (s, 9 H, Si$^t$BuMe$_2$), 0.18, 0.16, −0.25, −0.32 (singlets, 3 H each, Si$^t$BuMe$_2$); IR (CHCl$_3$) ν$_{max}$ 2957, 2930, 2858, 1471, 1438, 1258, 1220, 1097, 839 cm$^{-1}$; $^{13}$C NMR (125 MHz, CDCl$_3$) δ 137.2–125.7 (several signals, aromatic), 65.3 (CH$_2$O), 64.8 (CH$_2$O), 43.6 ($^1$J$_{cp}$=67.9 Hz, Ar—CH(-P=O), 26.1 (Si$^t$BuMe$_2$), 25.7 (Si$^t$BuMe$_2$), 18.7 (Si$^t$BuMe$_2$), 18.1 (Si$^t$BuMe$_2$), −5.1, −5.1, −5.8, −5.9 (Si$^t$BuMe$_2$); UV (EtOH) λ$_{max}$ 233 nm (ε 50,000); HRMS calcd for C$_{37}$H$_{52}$O$_3$PSi$_2$ (M⊕+1): 631.3192, found: 631.3157.

EXAMPLE 7

3-Iodo-2-naphthyl Alcohol (Compound 7)

To 500 ml of methanol (MeOH) and 50 ml of acetyl chloride were added 11.950 g (63.83 mmol) of 3-amino-2-naphthoic acid in 100 ml of MeOH. To this mixture were added 50 ml of benzene and 50 ml of CH$_2$Cl$_2$, and the reaction was stirred at room temperature for two hours and then at reflux for three hours. Then MgSO$_4$ was added and the reaction was heated at reflux for 12 hours. The MgSO$_4$ was replaced with 3 Å molecular sieves, and the reaction mixture was heated to reflux for 48 hours. The reaction mixture was then diluted with 500 ml of ethyl acetate (EtOAC), washed with 100 ml of saturated NH$_4$Cl, 100 ml of saturated NaHCO$_3$, 100 ml of 5 percent Na$_2$CO$_3$, brine, dried over MgSO$_4$ and concentrated. The product was purified by column chromatography (10 percent ether in petroleum ether) to give 7.412 g (36.83 mmol) of the aminonaphthoic ester (58 percent yield).

To 0.500 g (2.500 mmol) of the above ester in 25 ml of CH$_2$Cl$_2$ was added 10 ml of DIBAL (1M in hexanes) at −78° C., and the reaction mixture was warmed to room temperature. To the reaction mixture were added 20 ml of MeOH, 50 ml of EtOAC and 20 ml of Rochelle's salt. The organic layer was washed with saturated ammonium chloride, dried over MgSO$_4$ and concentrated. The product was recrystallized from toluene to yield 0.255 g (1.472 mmol) of 3-amino-2-naphthyl alcohol (59 percent yield).

The above aminonaphthyl alcohol (1.340 g; 7.736 mmol) in 13 ml of 6M sulfuric acid was heated to form a solution and then cooled to zero degrees C. To the resulting suspension were added 0.587 g (8.510 mmol) of NaNO$_2$ in 2 ml of water, and the reaction mixture was stirred at zero degrees C. for 10 minutes. Then, 0.200 g of urea in 2 ml of water were added at zero degrees C., with stirring for 5 minutes, followed by 1.926 g (11.604 mmol) of KI in 2 ml of water at zero degrees C. with stirring at room temperature for 15 minutes. A 50 ml portion of 1:1 ether-ethyl acetate, and 20 ml of saturated ammonium chloride and 20 ml of sodium bisulfate were added, the organic layer was separated and washed with ammonium chloride, sodium bicarbonate and brine, and then dried over MgSO$_4$. The product was purified by column chromatography (30 percent ether in petroleum ether) to give 0.585 g (27 percent yield) of 3-iodo-2-naphthyl alcohol.

Compounds 10, 14, 3a, 3b and 18a were prepared analogously to Compounds 8, 12, 1a, 16 and 16a using 3-iodo-2-naphthyl alcohol, Compound 7, in place of Compound 5. Data relating to Compounds 14, 3a, 3b and 18a are provided below.

Compound 14

Pale yellow oil; R$_f$=0.64 (silica, 60 percent ether in petroleum ether); $^1$H NMR (500 MHz, CDCl$_3$) δ 8.15 (s, 1 H, aromatic), 7.99 (s, 1 H, aromatic), 7.83 (m, 1 H, aromatic), 7.77 (m, 1 H, aromatic), 7.50 (m, 2 H, aromatic), 6.01 (s, 1 H, CHOH), 4.63 (s, 2 H, Ar—C≡C—CH$_2$O), 4.44 (bs, 2 H, CHOH—C≡C—CH$_2$O), 2.85 (bs, 1 H, CHOH), 0.97 (s, 9 H, Si$^t$BuMe$_2$), 0.91 (s, 9 H, Si$^t$BuMe$_2$), 0.20 (s, 6 H, Si$^t$BuMe$_2$), 0.13 (s, 3 H, Si$^t$BuMe$_2$), 0.12 (s, 3 H, Si$^t$BuMe$_2$); IR (CHCl$_3$) ν$_{max}$ 3592, 2960, 2931, 2859, 1472, 1368, 1257, 1101, 1078, 838 cm$^{-1}$; $^{13}$C NMR (125 MHz, CDCl$_3$) δ 138.3 (aromatic), 133.0 (aromatic), 132.8 (aromatic), 132.6 (aromatic), 128.1 (aromatic), 127.4 (aromatic), 127.1 (aromatic), 126.9 (aromatic), 126.1 (aromatic), 118.7 (aromatic), 92.8 (acetylene), 85.6 (acetylene), 83.8 (acetylene), 82.4 (acetylene), 63.2 (CHOH), 52.3 (CH$_2$O), 51.9 (CH$_2$O), 25.8 (Si$^t$BuMe$_2$), 18.3 (Si$^t$BuMe$_2$), 18.3 (Si$^t$BuMe$_2$), −5.1 (Si$^t$BuMe$_2$), −5.1 (Si$^t$BuMe$_2$); UV (EtOH) λ$_{max}$ 278 (ε 6,900), 250 (ε 54,500), 241 nm (ε 44,000).

Compound 3a

Pale yellow oil; R$_f$=0.48 (silica, ether); $^1$H NMR (500 MHz, CDCl$_3$) δ 7.87 (s, 1 H, aromatic), 7.86–7.76 (m, 4 H, aromatic), 7.71 (d, J=7.9 Hz, 1 H, aromatic), 7.64 (d, J=7.6 Hz, 1 H, aromatic), 7.52 (m, 2 H, aromatic), 7.44 (m, 4 H, aromatic), 7.34 (m, 1 H, aromatic), 7.28 (m, 2 H, aromatic), 6.89 (dt, J=10.7, 2.9 Hz, 1 H, CH=C=), 4.66 (m, 2 H, =C(P=O)—CH$_2$O), 4.58 (s, 2 H, ≡C—CH₂O), 0.96 (s, 9 H, Si$^t$BuMe₂), 0.79 (s, 9 H, Si$t$BuMe2), 0.18 (s, 3 H, SitBuMe₂), 0.17 (s, 3 H, Si$^t$BuMe₂), −0.02 (s, 6 H, Si$^t$BuMe₂); IR (CHCl₃) $\nu_{max}$ 2957, 2931, 2858, 1939, 1472, 1438, 1364, 1257, 1181, 1105, 1086, 838 cm⁻¹; ¹³C NMR (125 MHz, CDCl₃) d 210.4 (²Jccp=5.1 Hz, CH=C=C), 132.8-119.0 (twenty-two signals, aromatic), 103.6 (¹Jcp=99.3 Hz, CH=C=C), 96.2 (³Jcccp=13.1 Hz, CH=C=C), 92.4 (acetylene), 82.6 (acetylene), 60.6 (²Jccp=10.6 Hz, =C(P=O)—CH₂O), 52.3 (≡C—CH₂O), 25.8 (Si$^t$BuMe₂), 25.7 (Si$^t$BuMe₂), 18.3 (Si$^t$BuMe₂), 18.2 (Si$^t$BuMe₂), −5.0 (Si$^t$BuMe₂), −5.5 (Si$^t$BuMe₂) −5.5 (Si$^t$BuMe₂); UV (EtOH) $\lambda_{max}$ 267 (ε 57,000), 226 nm (ε 38,000); HRMS calcd for C₄₁H₅₂O₃PSi₂ (M⊕+1): 679.3192, found: 679.3169.

Compound 3b

Pale yellow oil, R$_f$=0.28 (silica, ethyl acetate); ¹H NMR (500 MHz, CDCl₃) δ 7.86 (s, 1 H, aromatic), 7.80 (m, 2 H, aromatic), 7.66 (m, 3 H, aromatic), 7.59-7.47 (m, 4 H, aromatic), 7.37 (m, 2 H, aromatic, 7.27 (s, 1 H, aromatic), 7.25-7.16 (m, 3 H, aromatic), 6.42 (bd, J=10.6 Hz, 1 H, CH=C=), 4.59 (d, J=16.7 Hz, 1 H, ≡C—CH₂OH), 4.51 (m, 2 H, =C(P=O)—CH₂OH), 4.49 (d, J=16.7 Hz, 1 H, ≡C—CH₂OH); IR (CHCl₃) $\nu_{max}$ 3349, 3011, 2961, 2930, 2857, 1936, 1438, 1214, 1120, 1099, 1028 cm⁻¹; ¹³C NMR (125 MHz, CDCl₃) δ 211.2 (CH=C =C), 134.3-119.0 (fifteen signals, aromatic), 101.4 (¹Jcp=97.6 Hz, CH=C=C), 96.9 (³Jcccp=12.9 Hz, CH=C=C), 94.7 (acetylene), 83.6 (acetylene), 61.1 (²Jccp=7.1 Hz, =C(P=O)—CH₂OH), 51.4 (≡C—CH₂OH); UV (EtOH) $\lambda_{max}$ 266 (ε 46,000), 224 nm (sh, ε 22,000); HRMS calcd for C₂₉H₂₃O₃PCs (M⊕+Cs): 583.0438, found: 583.0471.

Compound 18a

Pale yellow oil, R$_f$=0.51 (silica, ethyl acetate); ¹H NMR (500 MHz, CDCl₃) δ 8.46 (d, J=1.8 Hz, 1 H, aromatic), 8.37 (s, 1 H, aromatic), 8.28 (s, 1 H, aromatic), 7.94 (m, 4 H, aromatic), 7.79 (s, 1 H, aromatic), 7.52 (m, 5 H, aromatic), 7.41 (m, 2 H, aromatic), 7.14 (m, 1 H, aromatic), 7.06 (m, 2 H, aromatic), 4.89 (d, J=12.3 Hz, 1 H, Ar—CH₂O), 4.74 (d, J=12.3 Hz, 1 H, Ar—CH₂O), 4.44 (m, 2 H, Ar—CH(P=O), CH—CH₂O), 4.23 (m, 1 H, CH—CH₂O), 1.00 (s, 9 H, Si$^t$BuMe₂), 0.63 (s, 9 H, Si$^t$BuMe₂), 0.17, 0.16, −0.26, −0.34 (singlets, 3 H each, Si$^t$BuMe₂); IR (CHCl₃) $\nu_{max}$ 2957, 2929, 2857, 1471, 1438, 1258, 1117, 1097, 839 cm⁻¹; ¹³C NMR (125 MHz, CDCl₃) δ 137.0-125.2 (several signals, aromatic), 65.4 (CH₂O), 65.0 (CH₂O), 43.6 (¹Jcp=67.9 Hz, Ar—CH(P=O)), 26.2 (Si$^t$BuMe₂), 25.7 (Si$^t$BuMe₂), 18.7 (Si$^t$BuMe₂), 18.1 (Si$^t$BuMe₂), −5.0, −5.1, −5.8, −5.9 (Si$^t$BuMe₂); UV (EtOH) $\lambda_{max}$ 381 (ε 8,600), 263 nm (ε 81,000); HRMS calcd for C₄₁H₅₄O₃PSi₂ (M⊕+1): 681.3349, found: 681.3356.

Compounds 11, 15, 4a and 4b were prepared in a manner analogous to the preparation of Compounds 8, 12, 1a and 1b except that Compound 5 was reacted with phenylacetylene instead of the TBS-protected propargyl alcohol. Data relating to Compounds 15, 4a and 4b are provided below.

Compound 15

Pale yellow oil, R$_f$=0.45 (silica, 30 percent ether in petroleum ether); ¹H NMR (500 MHz, CDCl₃) δ 7.43 (m, 2 H, aromatic), 7.31 (m, 3 H, aromatic), 6.03 (dd, J=10.7, 8.9 Hz, 1 H, =CH—CHOH), 5.83 (d, J=10.7 Hz, 1 H, ≡C—CH=CH), 5.51 (m, 1 H, =CH— CHOH), 4.35 (d, J=0.9 Hz, 2 H, CH₂O), 2.16 (d, J=4.3 Hz, 1 H, CHOH), 0.88 (s, 9 H, Si$^t$BuMe₂), 0.10 (s, 6 H, Si$^t$BuMe₂); IR (CHCl₃) 8,27 $n_{max}$ 3596, 2957, 2931, 2859, 1490, 1472, 1257, 1131, 1077, 838 cm⁻¹; ¹³C NMR (125 MHz, CDCl3) δ 140.1 (C=CH—CHOH), 131.6 (aromatic), 128.6 (aromatic), 128.3 (aromatic), 122.7 (aromatic), 111.5 (CH=C—CHOH), 96.0 (acetylene), 84.5 (acetylene), 84.2 (acetylene), 83.5 (acetylene), 60.3 (CHOH), 51.8 (CH₂O), 25.8 (Si$^t$BuMe₂), 18.2 (Si$^t$BuMe₂), −5.1 (Si$^t$BuMe₂); UV (EtOH) $\lambda_{max}$ 291 (ε 13,500), 275 nm (ε 15,000).

Compound 4a

Pale yellow oil, R$_f$=0.40 (silica, ether); ¹H NMR (500 MHz, CDCl₃) δ 7.90 (m, 1 H, aromatic), 7.78-7.68 (m, 4 H, aromatic), 7.52-7.35 (m, 8 H, aromatic), 7.29 (m, 2 H, aromatic), 6.53 (dddd, J=10.7, 10.7, 2.7, 2.1 Hz, 1 H, CH=C=), 6.09 (ddd, J=10.7, 10.7, 1.8 Hz, 1 H, CH=CH—CH=), 5.54 (bdd, J=10.7, 3.0 Hz, 1 H, =C—CH=CH), 4.49 (m, 2 H, CH₂O), 0.79 (s, 9 H, Si$^t$BuMe₂), −0.04 (s, 6 H, Si$^t$BuMe₂); IR (CHCl₃) $\nu_{max}$ 2988, 2958, 2931, 2851, 1930, 1592, 1438, 1182, 1120, 1103, 838 cm⁻¹; ¹³C NMR (125 MHz, CDCl₃) δ 212.6 (²Jccp=4.4 Hz, CH=C=C), 132.6-128.3 (several signals, aromatic, =C—CH=), 123.0 (aromatic), 110.2 (⁴Jcccсp=4.8 Hz, CH=CH—CH=), 102.0 (¹Jcp=98.0 Hz, CH=C=C), 97.2 (acetylene), 95.3 (³Jcccp=13.0 Hz, CH=C=C), 85.6 (acetylene), 60.5 (²Jccp=10.6 Hz, CH₂O), 25.7 (Si$^t$BuMe₂), 18.2 (Si$^t$BuMe₂), −5.4 (Si$^t$BuMe₂), −5.5 (Si$^t$BuMe₂); UV (EtOH) $\lambda_{max}$ 328 (ε 17,000), 309 (ε 23,000), 222 nm (sh, ε 17,000); HRMS calcd for C₃₂H₃₆O₂PSi (M⊕+1): 511.2222, found: 511.2230.

Compound 4b

Pale yellow oil, R$_f$=0.32 (silica, ethyl acetate): ¹H NMR (500 MHz, CDCl3) δ 7.80-7.68 (m, 4 H, aromatic), 7.56-7.43 (m, 6 H, aromatic), 7.38 (m, 2 H, aromatic), 7.31 (m, 3 H, aromatic), 6.52 (bdd, J=10.7, 10.7 Hz, 1 H, CH=C=), 6.07 (ddd, J=10.7, 10.7, 1.8 Hz, 1 H, CH=CH—CH=), 5.59 (dd, J=10.7, 2.9 Hz, 1 H, =C—CH=CH), 4.50 (m, 2 H, CH₂O); IR (CHCl₃) $\nu_{max}$ 3360, 3020, 1929, 1592, 1490, 1439, 1210, 1168, 1121, 1070, 775 cm⁻¹; ¹³C NMR (125 MHz, CDCl₃) δ 213.5 (CH=C=C), 134.1-128.3 (several overlapping signals, aromatic, ≡C—CH=), 122.7 (aromatic), 111.3 (C=CH—CH=), 99.2 (CH=C=C), 97.7 (acetylene), 94.9 (³Jcccp=12.6 Hz, CH=C=C), 85.4 (acetylene), 60.7 (CH₂OH); UV (EtOH) $\lambda_{max}$ 307 (ε 14,000), 223 nm (sh, ε 18,000); HRMS calcd for C₂₆H₂₂O₂P (M⊕+1): 397.1357, found: 397.1376.

Although the present invention has now been described in terms of certain preferred embodiments, and exemplified with respect thereto, one skilled in the art will readily appreciate that various modifications, changes, omissions and substitutions may be made without departing from the spirit thereof.

We claim:

1. A diphenyl-(1,8-disubstituted-octa-2,3,5-trien-7-yne)phosphene oxide of the structural formula

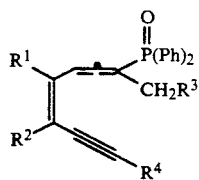

wherein
Ph is phenyl;
$R^1$ and $R^2$ are hydrogen or $R^1$ and $R^2$ together with the unsaturated carbon atoms bonded thereto form a mono- or bicyclic aromatic ring;
$R^3$ is hydroxyl or $C_1$–$C_6$ acyloxy; and
$R^4$ is hydroxymethyl, $C_1$–$C_6$ acyl hydroxymethyl or phenyl.

2. The phosphene oxide according to claim 1 wherein $R^1$ and $R^2$ together with the unsaturated carbon atoms bonded thereto form a mono- or bicyclic aromatic ring that is selected from the group consisting of a substituted or unsubstituted benzene, naphthalene, pyridine, quinoline, isoquinoline, pyrazine, quinoxaline, benzofuran, furan, thiophene, oxazole, pyrimidine, benzothiophene, isobenzofuran, isobenzothiophene, N-$C_1$–$C_6$ alkyl indole, N-$C_1$–$C_6$ alkyl isoindole, N-$C_1$–$C_6$ alkyl benzimidazole, and benzoxazole, said substituted mono- or bicyclic aromatic ring having a substituent selected from the group consisting of $C_1$–$C_6$ alkyl, hydroxyl, $C_1$–$C_6$ alkoxy, $C_1$–$C_6$ acyloxy, nitro and halo other than iodo.

3. The phosphene oxide according to claim 2 wherein said aromatic ring system is benzene or naphthalene.

4. 2-Diphenylphosphoroso-nona-2,3,5-trien-7-yne-1,9-diol.

5. 2-Diphenylphosphoroso-8-phenyl-octa-2,3,5-trien-7-yn-1-ol.

6. 1-(3-Diphenylphosphoroso-4-hydroxy-but-1,2-dienyl)-2-(3-hydroxy-prop-1-ynyl)benzene.

7. 2-(3-Diphenylphosphoroso-4-hydroxy-but-1,2-dienyl)-3-(3-hydroxy-prop-1-ynyl)naphthalene.

8. A pharmaceutical composition comprising a pharmaceutically effective amount of a diphenyl-(1,8-disubstituted-octa-2,3-5-trien-7-yne)phosphene oxide dispersed in a physiologically tolerable diluent, the substituted phosphene oxide having the structural formula

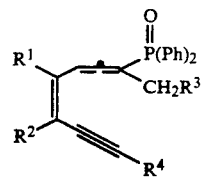

wherein Ph is phenyl;
$R^1$ and $R^2$ are hydrogen or $R^1$ and $R^2$ together with the unsaturated carbon atoms bonded thereto form a mono- or bicyclic aromatic ring;
$R^3$ is hydroxyl or $C_1$–$C_6$ acyloxy; and
$R^4$ is hydroxymethyl, $C_1$–$C_6$ acyl hydroxymethyl or phenyl.

9. The pharmaceutical composition according to claim 10 wherein $R^1$ and $R^2$ together with the unsaturated carbon atoms bonded thereto form a mono- or bicyclic aromatic ring that is selected from the group consisting of benzene, naphthalene, pyridine, quinoline, isoquinoline, pyrazine, quinoxaline, benzofuran, furan, thiophene, oxazole, pyrimidine, benzothiophene, isobenzofuran, isobenzothiophene, N-$C_1$–$C_6$ alkyl indole, N-$C_1$–$C_6$ alkyl isoindole, N-$C_1$–$C_6$ alkyl benzimidazole, and benzoxazole.

10. The pharmaceutical composition according to claim 8 wherein said aromatic ring system is benzene or naphthalene.

11. The pharmaceutical composition according to claim 8 wherein the phosphene oxide is selected from the group consisting of 2-diphenylphosphoroso-nona-2,3,5-trien-7-yne-1,9-diol, 2-diphenylphosphoroso-8-phenyl-2,3,5-trien-7-yn-1-ol, 1-(3-diphenylphosphoroso-4-hydroxy-but-1,2-dienyl)-2-(3-hydroxy-prop-1-ynyl)benzene and 2-(3-diphenylphosphoroso-4-hydroxy-but-1,2-dienyl)-3-(3-hydroxy-prop-1-ynyl)-naphthalene.

* * * * *